United States Patent [19]

Avrin et al.

[11] Patent Number: 5,842,986
[45] Date of Patent: Dec. 1, 1998

[54] FERROMAGNETIC FOREIGN BODY SCREENING METHOD AND APPARATUS

[75] Inventors: William F. Avrin; Peter V. Czipott; R. Kemp Massengill, all of San Diego, Calif.

[73] Assignees: Proton Sciences Corp., Escondido; Quantum Magnetics, Inc., San Diego, both of Calif.

[21] Appl. No.: 670,393

[22] Filed: Jun. 25, 1996

[51] Int. Cl.⁶ ........................................................ A61B 5/05
[52] U.S. Cl. ............................................ 600/407; 324/67
[58] Field of Search .............................. 128/653.1, 653.2, 128/899; 324/261, 260, 207.11, 207.13, 67; 340/551, 552; 623/11; 600/407, 410

[56] References Cited

U.S. PATENT DOCUMENTS

| | | | |
|---|---|---|---|
| 4,431,005 | 2/1984 | McCormick | 128/656 |
| 4,709,213 | 11/1987 | Padhrasky | 324/329 |
| 5,057,095 | 10/1991 | Fabian | 604/362 |
| 5,099,845 | 3/1992 | Besz et al. | 128/653.1 |
| 5,105,829 | 4/1992 | Fabian et al. | 128/899 |
| 5,107,862 | 4/1992 | Fabian et al. | 128/899 |
| 5,188,126 | 2/1993 | Fabian et al. | 128/899 |
| 5,190,059 | 3/1993 | Fabian et al. | 128/899 |
| 5,353,807 | 10/1994 | DeMarco | 128/772 |
| 5,425,382 | 6/1995 | Golden et al. | 128/899 |
| 5,456,718 | 10/1995 | Szymaitis | 623/11 |
| 5,494,033 | 2/1996 | Buchanan et al. | 128/653.1 |
| 5,558,091 | 9/1996 | Acker et al. | 128/653.1 |

OTHER PUBLICATIONS

Bastuscheck, C. M., *Technique for Measuring the AC Susceptibility of Portions of the Human Body or Other Large Objects*; J. Appl. Phys. 58 (10); Nov. 1985; pp. 3896–3906.

Bryden, F.M.; *Real Time Ultrasound in the Assessment of Intraocular Foreign Bodies*; Eye 4; 1990; pp. 727–731.

Costa Monteiro, E.; *Magnetic Measurement Techniques for Locating Foreign Bodies in Humans*; Tenth International Conference on Biomagnetism; Feb. 1996; p. 314.

Finn, Edward J.; *Ferromagnetic Materials in Patients*: Detection before MR Imaging; Radiology 156; Jan., 1985; pp. 139–141.

Greenblatt, R.E.; *Probablistic Reconstruction of Multiple Sources in the Bioelectromagnetic Inverse Problem*; Inverse Problems 9; Mar., 1992; pp. 271–284.

Kanal, Emanuel; *Aneurysm Clip Testing for Ferromagnetic Properties: Clip Variability Issues*; Radiology; Sep. 1995; pp. 576–578.

Mentor Corporation; *The Detector, Injection Port Detection System*; brochure; Oct., 1996; 6 pages.

Paulson, D. N.; *Biomagnetic Susceptometer with SQUID Instrumentation*; IEEE Transactions on Magnetics, vol. 27 No. 2; Sep., 1990; pp. 3249–3252.

Paulson, D. N.; *The Hamburg Biosusceptometer for Liver Iron Quantification*; Advances in Biomagnetism; date unknown; pp. 497–500.

Sekihara, Kensuke; *Reduction of Brain Noise Influence in Evoked Neuromagnetic Source Localization Using Noise Spatial Correlation*; Phys. Med. Biol. 39; Oct. 1993; pp. 937–946.

(List continued on next page.)

*Primary Examiner*—Marvin M. Lateef
*Assistant Examiner*—Eleni Mantis Mercader
*Attorney, Agent, or Firm*—Gerald W. Spinks

[57] ABSTRACT

A method and apparatus are disclosed for applying a low strength, time varying magnetic field to a selected screening region of a host, and for sensing a responsive magnetic field from a retained ferrous body within the screening region. The excitation field coil is designed to create a region of finite magnetic field within the screening region, and a region of near zero magnetic field. The sensors are placed within the region of near zero magnetic field to minimize the effect of the applied field. The effects of the applied field are further reduced by use of a reference sensor, field compensation coils, and a feedback loop. The magnetic gradient measured by the sensors is processed to locate and characterize the ferrous body.

8 Claims, 3 Drawing Sheets

OTHER PUBLICATIONS

Sepulveda, Nestor; *Magnetic Susceptibility Tomography for Three–Dimensional Imaging of Diamagnetic and Paramagnetic Objects*; IEEE Transactions on Magnetics, vol. 30, No. 6; Jun. 1993; pp. 5062–5069.

Shellock, Frank G.; *Magnetic Resonance, Bioeffects, Safety, and Patient Management*; 1996; pp. 115–126.

Smith, Neil; *A High–Sensitivity Magnetoresistive Magnetometer*; J. Appl. Phys. 69 (8); Apr., 1991; pp. 5082–5084.

Scholz, Bernhard; *Probability–Based Current Dipole Localization from Biomagnetic Fields*; IEEE Transactions on Biomedical Engineering, vol. 41 No. 8; Aug., 1993; pp. 735–742.

Wynn, W. M.; *Advanced Superconducting Gradiometer/Magnetometer Arrays and a Novel Signal Processing Technique*; IEEE Transactions on Magnetics, vol. MAG–11 No. 2; Sep., 1974; pp. 701–707.

FERROMAGNETIC FOREIGN BODY SCREENING METHOD AND APPARATUS

FIELD OF INVENTION

The present invention is in the field of detection of foreign bodies within a host through non-destructive methods. More specifically, the present invention involves the detection of ferromagnetic bodies within a host material having a different magnetic susceptibility.

BACKGROUND OF THE INVENTION

Industrial uses for metal detection systems include airport inspection for concealed weapons, mine detection and other military applications, as well as for the detection of traffic. Up to this time, metal detection systems have had little or no practical value for medical uses. This situation has changed substantially, however, now that Magnetic Resonance Imaging (MRI) scanning has become the premiere vehicle for noninvasive disease detection.

MRI scanning is used widely to evaluate diseases and injuries in the head. The sensitivity of MRI neurodiagnostic evaluation for brain tumors and other serious intracranial diseases is of such a high order that alternative older tests for such patients, such as X-rays and CAT scans, are rapidly becoming obsolete. In many parts of the United States, the MRI is now the preferred standard of care, and failure to prescribe MRI scanning can often be considered questionable. This revolutionary technology, however, is not without an inherent risk.

The particular risk addressed here, and in fact the most dangerous risk associated with MRI scanning, arises when ferrous metallic foreign objects reside in or near the eye or the brain of the patient. MRI systems use intense magnetic fields, typically one tesla (1T) or higher. When the magnetic field of the MRI system is applied, large forces are exerted on any ferromagnetic foreign body (FFB) within the magnetic field, and the ferromagnetic object tends to move. An elongated FFB can experience a strong torque, causing it to rotate. Such movement wreaks havoc on vital ocular or neurological structures. The most devastating effect of a ferrous metal object within the brain or the eye is the torque effect induced by the MRI magnetic field upon the ferrous object. Objects that are spherical do not rotate in the MRI magnetic field; however, most objects are not spherical. Therefore, most objects will tend to align with the magnetic field. This alignment is akin to a "propeller" effect, which can result in cutting through ocular or neurological tissues.

In most areas of the body, although damage can occur, the damage tends to be less extensive, because the body forms scar tissues and essentially "encapsulates" the ferrous metallic foreign object. This "encapsulation" does not occur to any significant degree within the eye or the brain. The two main areas of risk for MRI scanning, then, are the eye and the brain. The eye can have retained ferrous metallic foreign objects which are subjected to forces or torque which pull or rotate the object through the ocular tissues, which could cause a permanent loss of sight. Obviously, welders and machinists are at a particularly high risk. The clinical literature contains case studies of patients with previously unknown intraocular FFB's suffering blindness during or after an MRI scan. Motion of the FFB can cause effects such as vitreous hemorrhage, retinal damage, or even severing of the optic nerve. A similar problem exists within the brain, since a retained intracranial ferrous metallic foreign object can be moved through brain tissue. Neurologic deficit can be a consequence.

In other areas of the body, where the ferrous metallic foreign object becomes embedded in fibrous tissue, the risk of catastrophically damaging movement during the MRI procedure is minimal. However, forces on some aneurysm clips can be sufficient to cause either dislodging from a vessel or damaging displacement even without dislodging, at magnetic fields from 0.147 to 1.44 T. Clips are relatively large, measuring from 6 to 39 mm in length. Discomfort can also occur with heating of the encapsulated ferrous metallic foreign object. This heating occurs through induction caused by the radio frequency fields and pulsed magnetic field gradients used in MRI procedures. Excessive local heating is a risk for larger metallic objects, at least. Burning has been known to occur around pacemaker devices, for example. Pacemaker devices also present the potentially life-threatening hazard of malfunctioning during the performance of an MRI scan.

As shown above, FFB's in the body of a patient can cause significant problems during MRI scanning. The problems are especially important in the eye and brain, and there are some problems in other areas as well. The significance of the problems encountered is caused largely by the size of the magnet used. A typical MRI system generates a magnetic field strength between 10,000 Oersted (Oe) and 15,000 Oe, or 1 to 1.5 T. Often, the field is produced by a superconducting magnetic coil system. The cryogenic coils cannot be readily switched, so the patient is either inserted into the MRI machine with the magnetic field turned on, or the field is incrementally increased after the patient is positioned within the MRI machine. In either case, the changing magnetic field imposes a torque on any retained FFB, causing a rotational movement of the object. This torquing effect obviously occurs when the MRI scans the body region where the ferrous object is located, but it can also occur when other body regions are scanned. The magnetic field of the MRI system is very large, extending for a distance of several feet. Thus, for example, when the knee is scanned, a large magnetic field is applied not only to the knee, but also to the eye and brain. So, even during MRI scanning of the knee, torquing of an FFB in the eye can occur.

Damage can arise not only in conventional MRI units with magnetic field strengths of 1 T or higher, but also in units with field strengths as low as 0.35 T. Laboratory studies with freshly harvested animal or cadaver eyes have found that intraocular and intraorbital FFB's show the most significant movement during an MRI procedure using fields from 1 to 1.5 T in strength. These studies used implanted FFB's ranging in size from 1×2×0.5 mm to 1×9×9 mm to 5×5×7 mm. The strong consensus in the literature is that the risk of trauma from retained FFB's for metal workers is sufficient to withhold MRI, at least at field strengths greater than 0.35 T, in the absence of a screening test.

Attempts have been made to reduce the risk associated with retained ferrous metallic objects by constructing MRI machines with still lower magnetic fields, for instance, about 3000 Oe (0.3 T) or lower. These attempts have resulted in either a degradation of the final image or a prolonged exposure of the patient to the MRI field. Prolonged exposure can be particularly stressful for patients who suffer from claustrophobia, since many MRI systems enclose the patient. MRI systems operating at fields as low as 0.08 T and 0.06 T nearly eliminate the risk of ocular damage. However, the spatial resolution of images taken at such low fields is generally considered unacceptable. Therefore, such attempts at reducing the risk by reducing the magnetic field strengths have had suboptimal results.

Another option is to avoid the risk associated with retained ferrous objects by avoiding the performance of MRI procedures on a patient who is known to have such a foreign object in a high risk location. Avoidance of the risk in this manner is complicated by a frequent lack of vital information for the radiologist. The presence of ferrous metallic foreign objects in the eye, the orbit, the head, the chest, or other vital areas of the body, is a well known contraindication for MRI procedures. However, a patient often does not know that the foreign object is present, or the patient does not provide such information to the radiologist. Therefore, radiologists performing MRI scanning may be unaware that a patient has a retained ferrous metallic foreign object, with potentially catastrophic consequences. Ocular damage, with permanent visual loss, has occurred as a result of MRI scanning in such instances.

Risk determination with medical procedures is often difficult. Physicians must daily weigh the costs and risks of diagnostic procedures against the information gained, often with inadequate information as to the probability of an adverse reaction. In the case of MRI, a low-cost, low-risk screening procedure to detect FFBs would allow physicians to make this decision in an informed way, avoiding the risk of damage without depriving patients needlessly of a vital diagnostic modality.

Several procedures have been investigated for their applicability as pre-MRI screening procedures. In fact, the MRI procedure itself has been investigated extensively for its ability to provide images of intraorbital and intraocular foreign bodies. However, the MRI procedure itself is obviously unsuitable as a screening procedure except at very low magnetic fields. At such fields, the sensitivity of the MRI procedure is too low to detect many objects. In addition, since most existing MRI systems run at fixed magnetic fields, low-field screening with an MRI scan would have to be done with a separate MRI instrument. The cost of even an ultralow-field MRI instrument would be unacceptably high for routine screening.

X-ray radiography has shown mixed results in detecting foreign bodies near the eye. Some success has been experienced with larger objects, but some failures have also been recorded. Computed tomography (CT) is generally considered superior to simple radiography in detection of foreign bodies. Some studies have claimed highly reliable detection of bodies as small as 0.06 mm$^3$, showing that CT scans can readily detect objects missed by radiography. However, some case studies have also shown failure of CT to detect even a significant steel object in the eye. Furthermore, the CT procedure is too expensive for routine screening. Both CT scans and simple X-ray radiography share another serious problem, in that they can differentiate between metallic and nonmetallic bodies, but not between ferromagnetic and non-ferromagnetic bodies. If these techniques were relied upon to withhold MRI procedures, this deficiency would lead to the needless denial of MRI procedures to some patients with retained non-ferromagnetic foreign bodies. If all patients having retained metallic objects were denied the application of MRI scanning, many of those patients would be needlessly deprived of a valuable diagnostic procedure. To base a clinical decision to perform or not to perform an MRI based on plain X-ray films showing a metallic foreign body is highly undesirable, as the X-ray does not answer vital questions regarding the ferrous composition of the retained metallic foreign object. This problem, together with the need to use ionizing radiation, and the occasional failure to detect significant objects, makes X-ray and CT techniques unsuitable for pre-MRI screening.

Ultrasound is another method for detecting foreign bodies in or near the eye. One study has found that ultrasound had a probability of detection, for all types of foreign body materials, of 93%, as compared to 40% for simple radiography. The detection rate rivals that of CT for intraocular foreign bodies, but falls short of CT for extraocular bodies in parts of the orbit. High-frequency ultrasound produces even clearer results. However, ultrasound procedures suffer the same deficiency as X-ray and CT procedures, in that they cannot distinguish ferromagnetic from non-ferromagnetic foreign bodies.

Passive magnetic detection, as used in magnetoencephalography (MEG), can detect the perturbation of the earth's magnetic field caused by a ferromagnetic object. Algorithms exist which allow localization and characterization of the object by measuring a complete set of magnetic field and gradient tensor components. However, the ultra-sensitive magnetometers used for MEG are exceedingly expensive. Furthermore, the static field perturbations caused by an FFB can be difficult to distinguish from background fields.

It would be advantageous to have a ferrous metal detection system designed to screen patients before the commencement of MRI scanning. With the rapid development of MRI scanning, such screening could reduce the morbidity and human suffering caused by MRI-induced movement of ferrous metallic foreign objects within or adjacent to vital organs.

In addition to the detection of retained ferrous metallic objects for pre-MRI screening, it would also be appropriate to provide a ferromagnetic detection capability to patients suffering from acute orbital and intraocular trauma. In many instances, nonferrous metallic foreign objects can be allowed to remain permanently within the orbit, minimizing iatrogenic surgical trauma. On the other hand, ferrous metallic foreign objects often require aggressive surgical removal, which is potentially more destructive than simply leaving a nonferrous metallic foreign object in place. A screening test which would minimize the surgical invasiveness required in a given clinical situation would be useful.

It is an object of the present invention to provide a method and apparatus for the detection of ferrous metallic objects retained within a selected region of a host. One type of host could be a patient being considered for MRI scanning. It is a further object of the present invention to provide a method and apparatus for determining the location and size of a retained ferrous metallic object within the body of a patient. It is a further object of the present invention to provide a method and apparatus for discriminating between ferrous and nonferrous retained metallic objects within the body of a patient. Finally, it is an object of the present invention to provide a method and apparatus for detection, location and characterization of a retained metallic object, which are noninvasive and safe, as well as economical and easy to use.

SUMMARY OF THE INVENTION

The present invention utilizes magnetic susceptibility measurement to accomplish the detection of retained ferrous metallic objects inside human tissue, as a means of screening patients prior to MRI and other medical procedures. It also can include the application of a combination of one or more magnetic measurement techniques, to enhance the accuracy, reliability, and economy of the screening process.

A field generating device is placed near the body region to be screened. The field generating device consists of one or more devices for generating a time-varying applied magnetic field. A sensor or array of sensors is also positioned adjacent to the body region to be screened. Signals from the sensors indicate the presence of any ferrous magnetic objects in the selected body region. Together, the field generating device and the sensor allow measurement of anomalies in the magnetic susceptibility of the body region being screened. Sensors can be stationary, or they can be movable to generate a magnetic susceptibility anomaly map over the body part being screened. The intensity and the time dependence or frequency dependence of the magnetic susceptibility anomaly can be interpreted rapidly by a computer processor to reveal the location and size of ferrous metallic objects retained within the screened body region.

Stationary magnetic sensors can measure an appropriate combination of magnetic field gradients, and subsequent processing of the sensor output signals with the well known Frahm-Wynn algorithm can locate and characterize the retained ferrous objects. Alternatively, a moving sensor or sensor array is mounted on a position-encoding fixture, and sensor and position encoder outputs are transmitted to a computer where they are analyzed to provide the desired information.

The novel features of this invention, as well as the invention itself, will be best understood from the attached drawings, taken along with the following description, in which similar reference characters refer to similar parts, and in which:

DESCRIPTION OF PREFERRED EMBODIMENTS

The method of alternating current magnetic susceptibility measurement combines all the advantages of the prior art screening procedures described above, with none of their drawbacks. In this technique, an alternating magnetic field is applied to the selected region of the host, which is to be screened. Metallic bodies in the selected region will respond to the applied field, producing their own small alternating magnetic fields. These magnetic susceptibility anomalies are detectable using reasonably inexpensive sensors, and in contrast with passive magnetic measurements, the desired signals can be distinguished from background noise by synchronous detection. This is accomplished by measuring only the component of the responsive magnetic field that oscillates at the same frequency as the applied ac magnetic field.

Ferromagnetic metals can also be distinguished from non-ferromagnetic metals by the polarity and frequency dependence of the responsive magnetic signal. Ferromagnetic bodies have a paramagnetic susceptibility, in which the direction of the responsive magnetic moment is the same as the direction of the applied field. This susceptibility approaches a constant, non-zero value as the frequency of the applied field approaches zero. On the other hand, non-ferromagnetic metallic bodies display an eddy-current response, in which the direction of the responsive magnetic moment is opposite to the direction of the applied field. This non-ferromagnetic response approaches zero as the frequency of the applied field approaches zero. Therefore, a signal processor can discriminate between the two types of responses by making measurements at two or more frequencies and observing the change in the responsive magnetic moment.

Since this method will involve applying a magnetic field to the patient, this applied field is held sufficiently low to avoid causing injury. It has been found that an applied ac magnetic field of only 0.0001 to 0.01 T is sufficient for the practice of this method on a patient being considered for an MRI procedure. In the practice of this invention on other hosts, a different level of applied field might be necessary and sufficient. Fields of up to 0.01 T will not cause damage to the patient due to motion of FFBs. There is also little risk of inducing excessive electric fields, or excessive heating of metallic implants.

Since the applied magnetic field is very small, the responses from detected ferrous objects are also very small. A clinically useful tool must detect the ac magnetic response from the smallest ferromagnetic bodies that can produce trauma in the selected screening region of the patient, during MRI. A simple model can be used to estimate the size of the smallest signal which must be measured. In this model, the foreign body is a sphere whose magnetic susceptibility, normalized to the permeability of the surrounding medium, is much larger than one. If this spherical particle is exposed to a spatially uniform magnetic field, the magnetic field $B_{sig}$ produced by the sphere itself is given by the relation $$B_{sig} \approx B_{app} a^3 / r^3,$$

where $B_{app}$ is the applied field, a is the radius of the sphere, and r is the distance from the sphere to the magnetic sensor.

Placing the sensor close to the surface of the eye of the patient limits the distance from the sensor to any part of the orbit to a distance little greater than the diameter of the orbit. So, a reasonable value for r might be 5 cm. Studies estimating the minimum size of a particle which might be harmful suggest that a particle having a volume of 1 mm$^3$ would be a reasonable minimum size. A 1 mm$^3$ spherical particle would have a radius a of approximately 0.62 mm. A design value of 0.5 mm is selected, to provide a safety margin. With a=0.5 mm and r=5 cm, it follows that $B_{sig}/B_{app}=10^{-6}$.

The ability to detect these small signals depends on the magnitude of the applied field, the noise in the magnetic sensors, the noise from the magnetic environment, and the degree to which the effects of the applied field can be suppressed. As an example, an applied ac magnetic field of 10 oersteds ($10^{-3}$ T) can easily be applied to a head-sized volume, without dissipating excessive amounts of power in the ac field coils, or causing injury to the patient. Fields of this magnitude, oscillating at a frequency between 10 and 100 Hz, are no greater in intensity or rate of change than the time-varying magnetic gradient fields used in MRI procedures.

With an applied field of $10^{-3}$ T, the magnitude of the responsive magnetic field from the model particle will be approximately $10^{-9}$ T. Therefore, where it will be used with an applied field of 0.001 T, the present invention requires a magnetic sensor which is inexpensive but still sensitive enough to detect this small magnetic signal, which will be received from the small foreign bodies which are of most interest. It is desirable to use a resistor having a sensitivity of at least 100 pT/Hz$^{1/2}$ at 10 Hz, and preferably 10 pT/Hz$^{1/2}$ at 10 Hz. The preferred sensor for this application is an improved magnetoresistive (MR) sensor recently developed by Eastman Kodak. Magnetoresistive sensors are a well developed, reliable technology used mainly in the recording heads of computer disk drives. Recent developments have enabled the manufacture of MR sensors with the requisite sensitivity, on the order of 10 pT/Hz$^{1/2}$ at 10 Hz. The field produced by the model particle is at least ten times higher than the noise in the Kodak MR sensors, for a measurement bandwidth of one Hz. Therefore, even a few seconds of data-averaging time will push the sensor noise well below the signal strength of the particles of interest. A variety of other sensor types could also meet the requirements of the present invention in the appropriate applications, including fluxgate magnetometers and magnetotransistors.

In order to detect the small ac magnetic field from the retained foreign body, in the presence of the much larger applied ac field, it is necessary to suppress any fluctuations in the contribution that the applied field makes to the total measured field. Several strategies can be used, in various combinations, to suppress these applied-field fluctuations. First, a very stable applied field source is used, to ensure that the current in the applied-field coils is as constant as possible. Second, the applied ac magnetic field is created with a coil which is specially designed, so that the applied ac field has a first zone of nearly zero field strength at the location of the magnetic sensors, while having a second zone with a finite field strength in the selected region of the host being screened. Third, the difference is measured between the magnetic fields sensed by two or more sensors. The sensors are placed in symmetrical positions within the first zone of low field strength created by the applied-field coil, so that the ac field that they see is not only small, but nearly the same for both sensors. In this arrangement, the differential measurement between their signals tends to cancel out any effects of residual fluctuations of the applied field. Using these techniques, magnetic signals $10^8$ times smaller than the applied ac magnetic field have been measured. This level of applied-field rejection is more than sufficient to detect the sizes of foreign bodies that are of interest.

In addition to rejection of noise caused by the applied ac magnetic field, there are two additional advantages to measuring the spatial differences, or gradients, of the magnetic field. First, it cancels out most of the magnetic noise from the environment, since the closely spaced sensors see approximately the same background fields. By making magnetic gradient measurements, we can easily suppress the ambient noise by a factor of 10 to 100, helping to ensure that the magnetic signature of a small ferromagnetic particle can be measured in the anticipated environments. For example, if the applied field were $10^{-4}$ T, the model particle considered above would produce a magnetic field of $10^{-10}$ T. Even in fairly noisy environments, the ambient noise is typically less than $10^{-9}$ T, at least at frequencies well removed from the harmonics of the AC power frequency, 60 Hz. Suppressing this noise by a factor of 100 would keep the environmental noise contribution an order of magnitude smaller than the signature of the model particle.

Second, measuring magnetic-field gradients enables a faster method of locating the source of a magnetic signal, and demonstrating where the source lies within the selected region of the host, such as the eye or the orbit of a patient. This method involves measurement of all five independent components of the ferrous object's magnetic field gradient tensor $g \equiv ((\partial B_i / \partial X_j))$ at a given point. Then, the Frahm-Wynn algorithm, well known to those skilled in the art, is used to determine the location, magnitude, and orientation of a magnetic dipole source having this field. This approach eliminates or reduces the need to map the responsive ac magnetic field at a plurality of locations in space. Use of the Frahm-Wynn algorithm is discussed below in more detail.

One way to locate the source of a magnetic field is to move the magnetic sensor, take several measurements at different positions, map out the magnetic field as a function of position, and then calculate a source location which best fits the magnetic-field map. One difficulty of this field mapping is the need to reposition the sensor many times, accurately measuring its position each time.

An alternative way to locate the magnetic source is to measure all five independent components of the magnetic gradient tensor at a single position in space. The location of the source is then determined from this single data point, by using an algorithm developed by Frahm and Wynn. The magnetic gradient tensor is represented by a collection of nine numbers, corresponding to the derivatives of each of the three components of the magnetic field with respect to each of the three spatial coordinates. However, through the fundamental laws of electromagnetism, the different spatial derivatives of the magnetic field can be related to each other, so that the magnetic gradient tensor can be expressed in terms of only five mathematically independent components.

The Frahm-Wynn algorithm assumes that the source is a magnetic dipole. This assumption is valid as long as the physical dimensions of the source are small compared with the distance between the source and the sensor. This condition is usually well satisfied in situations for which the present invention is intended. For example, in screening the orbit of a patient, the goal is to locate a piece of metal of perhaps a millimeter or less in its major dimension, which will be several centimeters away from the magnetic sensors. If the source is assumed to be a magnetic dipole, the dipole can be completely described in terms of six independent quantities. They are: three quantities for the orientation and magnitude of the magnetic moment (two angles to define the direction, and a third quantity to define the magnitude), and three quantities for the direction and distance of the source from the sensor (two angles and a linear measurement).

Frahm and Wynn demonstrated that, if the magnetic gradient tensor of the source is measured at a single point, that measurement can be used to calculate five of the six independent quantities which describe the dipole. Those five quantities are the orientation of the magnetic moment (two angles defining a direction in space), the direction from the source to the sensor (two angles defining a direction in space), and the product of the magnetic moment and the fourth power of the distance from the source to the sensor (the fifth independent quantity). Using any additional independent piece of related information, the magnetic moment and the distance from the source to the sensor can be determined, thus completely locating and characterizing the magnetic dipole source. This additional piece of information needed to solve for magnetic moment and distance can be obtained by measuring one of the three components of the magnetic field, as opposed to its derivatives with respect to position, or by repeating the magnetic gradient measurement at an additional location in space.

Since the Frahm-Wynn algorithm involves solving a non-linear set of equations, it does not provide a unique solution for the dipole location and size. Instead, it provides four possible solutions, the correct one plus three "ghost" solutions. In the present application, it may be possible to eliminate the ghost solutions which lie outside the screening region, such as a patient's head. Alternatively, the ghost solutions can be eliminated by measuring the magnetic gradient tensor at two locations in space, and applying the Frahm-Wynn algorithm to each set of measurements. The common solution found in both cases would then be the correct solution.

The magnetoresistive sensor which is the preferred sensor for use in the present invention reflects a change in the magnetic field as a change in the resistance of the sensing element. The resistance of the sensing element is read with the use of a Wheatstone bridge, as is well known in the art. Combinations of these sensors are used in the present invention to measure a magnetic gradient of a source.

In measuring the magnetic gradient tensor, a technique called the Three Sensor Gradiometer (TSG), developed by IBM Research can be used. The TSG gives superior background noise rejection and eliminates the need to measure a small differential signal, by directly subtracting the much larger background signals common to both sensors.

The simplest way to make a magnetic gradient measurement is to subtract the outputs of two sensors. However, this requires each sensor to have sufficient dynamic range to be capable of reading the full amplitude of the background noise in addition to the signal of interest. The TSG eliminates this problem by using a third reference sensor to eliminate the effect of the background field. Two primary sensors optimized for low noise are used to detect the magnetic gradient component of interest. The reference sensor, optimized for wide range, is operated in a magnetic feedback loop to monitor the magnetic background. The feedback loop monitors the signal of the reference sensor and supplies a current to a field-cancellation coil surrounding the reference sensor. The feedback loop adjusts the current to the coil to maintain the reference sensor in a constant field, as measured by the output of the sensor. At the same time, this same current is applied to identical field cancellation coils surrounding the primary sensors. This cancels the effect of the background field on the primary sensors, leaving the primary sensors to sense the residual magnetic gradient of the source. The difference between the fields sensed by the primary sensors is given by the magnetic gradient multiplied by the separation between the sensors, called the baseline.

The version of the TSG used in the present invention can have two layers of magnetic feedback loops, a primary loop and a secondary loop. The first, or primary, layer is the reference sensor feedback loop described above. The secondary layer consists of a separate secondary feedback loop for each primary sensor. Each secondary feedback loop monitors the output of one of the primary sensors and supplies a small additional current to the field cancellation coil for that sensor, as needed to cancel out the magnetic field entirely, at that sensor. The magnetic gradient of the source is then measured by electronically subtracting the outputs of the two secondary feedback loops.

The discussion above is stated in terms of the first-order gradiometer, which uses two primary sensors to measure the difference in magnetic field between two points in space. Higher-order gradiometers use larger numbers of sensors to measure the higher order spatial gradients of the field. For example, a second order gradiometer uses three primary sensors to measure the second derivative of the magnetic field with respect to position. The basic principles of the TSG apply to gradiometers of any order.

The magnetic gradiometer is used to cancel out some undesired magnetic background field, such as the applied ac magnetic field in the present invention, or magnetic noise from the environment, while still detecting the magnetic signal produced by a retained ferromagnetic foreign body. The two primary sensors are arranged so that they see the same background fields, but one primary sensor sees the desired signal more strongly than the other. In such a situation, subtracting the outputs of the two sensors will cancel out most of the background signal but will not cancel out the signal from the FFB.

A key parameter in designing the magnetic gradiometer is the length of the gradiometer baseline, or distance between the two primary sensors. To reject the background noise as well as possible, the two primary sensors need to be close together, in one sense. For example, to reject background noise, the separation of the two primary sensors should be small compared with the distance from the magnetic gradiometer to the sources of background noise. Similarly, to reject the effect of the applied ac field in the present invention, the primary sensors should be close together, as compared to the dimensions of the coil system that produces the applied ac field. However, if the primary sensors are placed too close together, as compared to the distance from the sensors to the signal source of interest, the two primary sensors will see the desired signal with approximately the same amplitude. In such a situation, subtracting the outputs of the two sensors will nearly cancel out the signal received from the FFB. The best compromise between seeing the desired signal and rejecting the background noise is typically achieved by choosing a gradiometer baseline which has approximately the same magnitude as the distance between the gradiometer and the signal source of interest. In the case where the present invention is used to screen the orbit of a patient for FFB's, this distance will be on the order of 5 cm.

The apparatus used in the present invention includes the following: (1) a set of excitation coils for applying the ac magnetic field to the screening region, (2) a set of optimally arranged magnetic sensors, and (3) equipment for using magnetic measurement signals from the sensors to detect and locate ferromagnetic objects, and for distinguishing the signals of the target objects from other interfering magnetic fields.

The excitation coils and magnetic sensors are arranged to reduce the interfering signal produced by the applied magnetic field. This requires that the applied field experienced by the primary magnetic sensors must be both as small as possible, and as nearly the same for all sensors as possible. Further, in order to ensure the detection of long, narrow ferromagnetic objects oriented in all possible directions, magnetic response measurements must be made in at least two locations relative to the region being screened.

Figure 1:
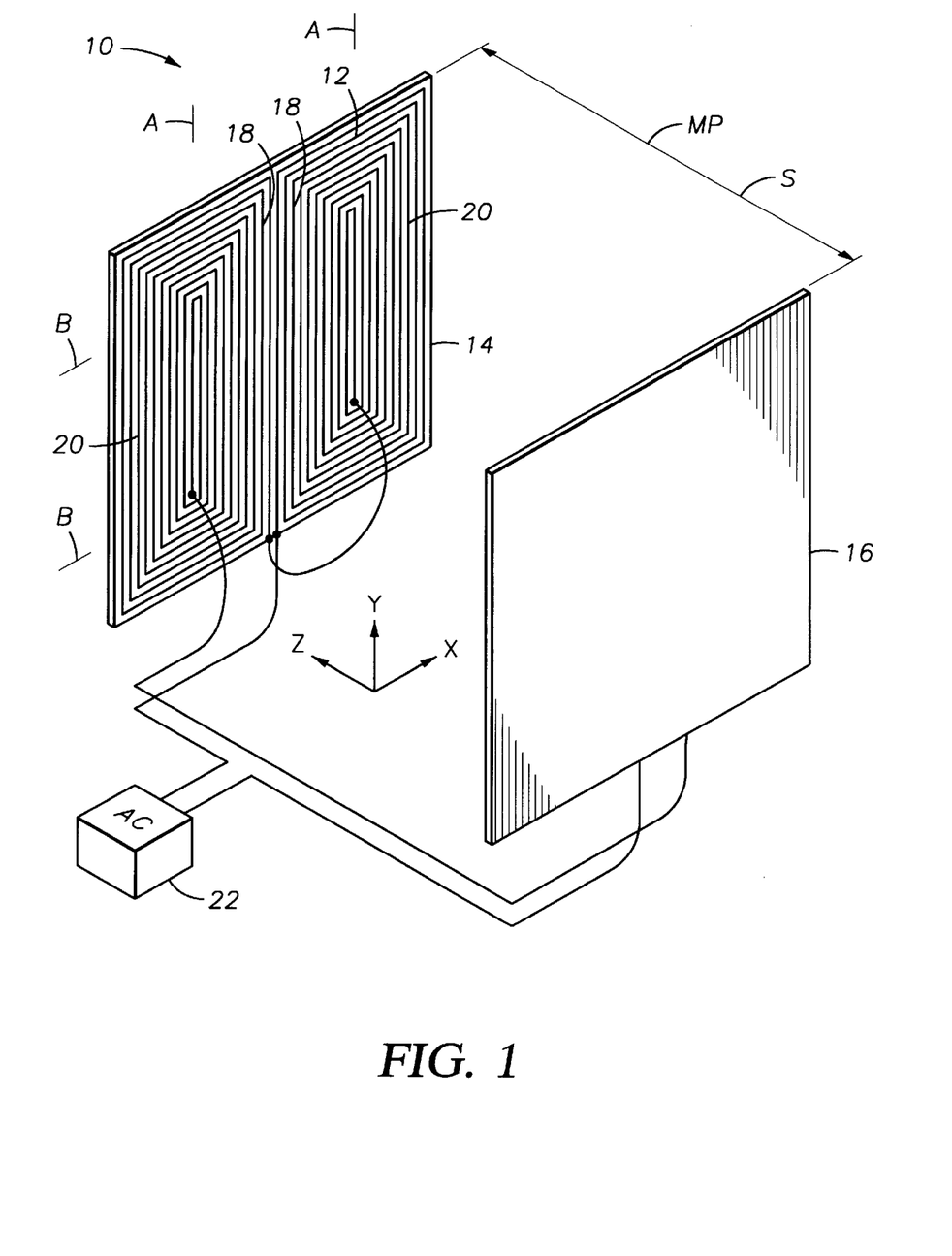
FIG. 1 is an expanded view of an excitation coil and sensor array as used in the present invention.

A key problem solved by the present invention is detection of the small ac magnetic signal produced by a minute ferromagnetic foreign body, in the presence of an ac excitation field that may be several orders of magnitude larger than the signal of the FFB. FIG. 1 shows one arrangement of the excitation device 10 used in the apparatus of the present invention, to solve this problem. One of the strategies used is to configure the excitation device 10 so that the ac excitation field is nearly canceled out in a region within the device 10, within which the magnetic sensors will be placed. The excitation-field coil 12 is laid out on the surfaces of two printed-circuit (PC) boards 14, 16. The two PC boards 14, 16 are placed parallel to each other, with the magnetic sensors placed between the two PC boards 14, 16. Each PC board 14, 16 accommodates a multiplicity of parallel, evenly spaced current paths 18 traveling in one direction in the center region of the board, with return paths 20 along the outer edges of the board, approximating two spiral patterns. The spiral patterns on one PC board are connected in series so that, when a current is passed through them, the resulting electric current distribution approximates a uniform sheet of current flowing in the y direction in the Figure, over a substantial region near the center of the board. This region of the board is roughly defined by the area between the markers A—A and between the markers B—B in the figure. This current distribution produces a magnetic field which is nearly uniform over a region of space near the center of the board.

Figure 2:
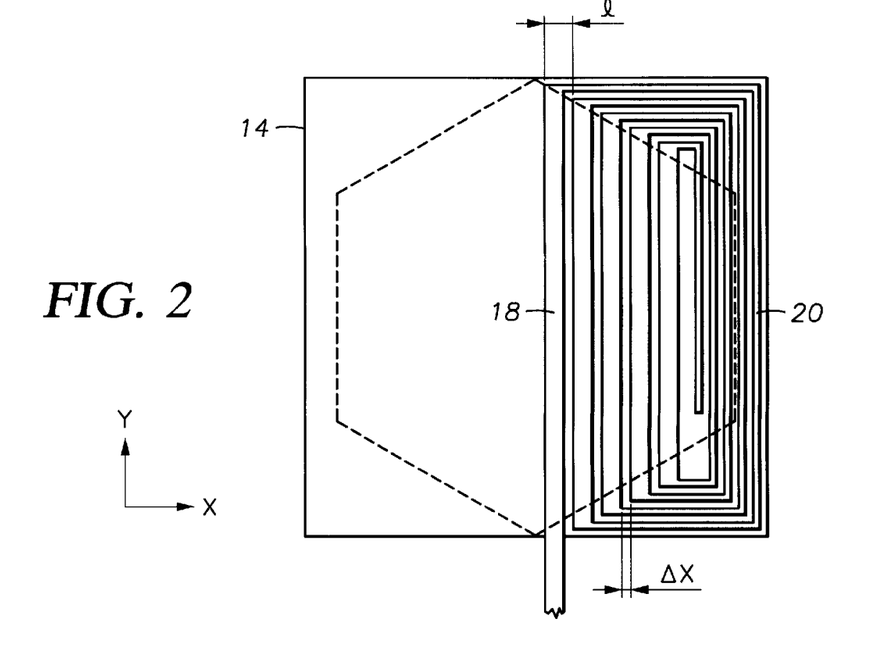
FIG. 2 is an elevation view of the excitation coil and sensor array of FIG. 1, as they would be used in screening a patient.

FIG. 2 illustrates that the region over which the uniform sheet of current exists is actually a six-sided region defined by the dashed line. This Figure also demonstrates one method of maximizing the size of this region of uniform current. The widths of the current paths 18 in the center of the board 14 can be increased, while the widths of the return paths 20 near the edge of the board 14 can be decreased. This enlarges the region covered by the uniform sheet of current to cover as much as possible of the PC board 14.

Returning to FIG. 1, it can be seen that two boards 14, 16 of this design are placed parallel to each other, with this relationship being shown in an expanded view in the Figure. In actuality, the PC boards 14, 16 are separated by a distance S which is small compared with the length and width of the central region of uniform current. The two PC boards 14, 16 are mounted so that the current paths 18 on one board are oriented parallel to the corresponding current paths 18 on the other board. The current paths on the two boards 14, 16 are then connected in series to an ac power supply 22, so that the current flows in the same direction on both boards, the y direction in the arrangement shown. The power supply 22 can be equipped with a control device, as is known in the art, to cause the field to be pulsed, to vary in frequency, or to have a waveform with multiple frequencies. These time variations in the applied field can assist in distinguishing the responsive field from the environmental background fields, by synchronization of the sensing circuitry with the power supply. In a region surrounding the centers of the two PC boards 14, 16, the magnetic field produced by this arrangement approximates that produced by a pair of parallel, uniform sheets of current flowing in the y direction. In the space between the centers of the two PC boards, the net magnetic field is nearly zero, since the contributions from the two current sheets approximately cancel each other. There is, however, a small residual magnetic field, since perfect field cancellation is prevented by the finite size of the regions of the current sheets, and the presence of the return paths 20 along the outer edges of the PC boards 14, 16. As will be discussed below, the magnetic sensors will be placed in a plane parallel to the PC boards 14, 16, with the plane of the sensors being located at the midpoint MP between the two PC boards 14, 16, so that the sensors will be in this near zero field.

Figure 3:
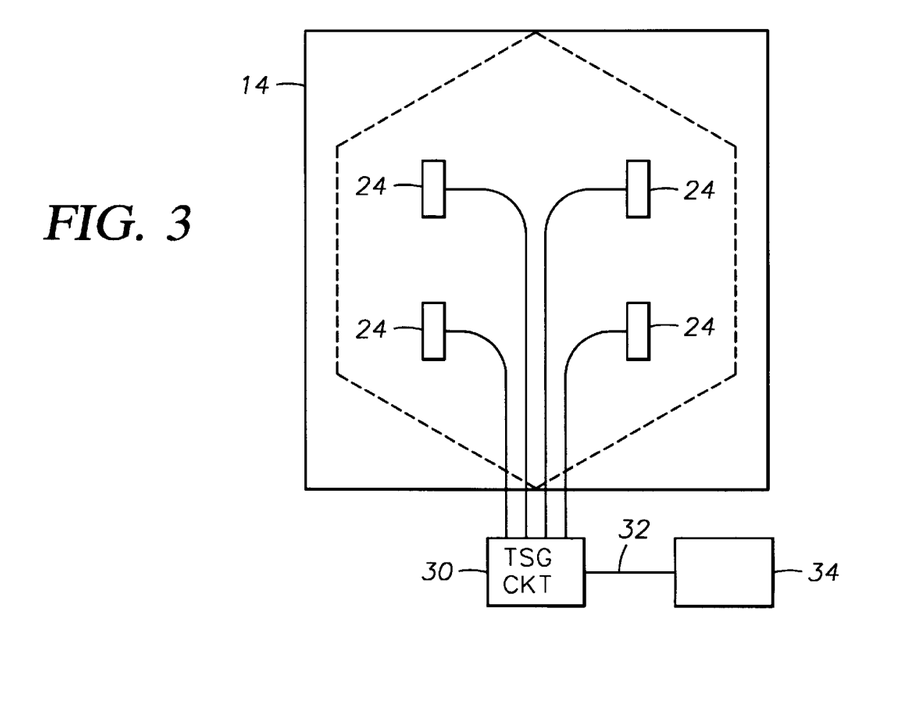
FIG. 3 is a plan view of a typical PC board, showing a typical placement of sensors.

FIG. 3 illustrates a typical PC board 14, with the region of the uniform current sheet shown by the dashed line. The magnetic sensors 24 are placed symmetrically with respect to the region of uniform current, so that the ac excitation field is nearly the same for each sensor 24. Further, since as mentioned above, the sensors 24 are placed in a plane midway between the PC boards 14, 16, the ac excitation field seen by each sensor 24 is not only uniform, but it is also near zero.

The magnetic fields at the locations of the sensors 24 must be spatially uniform, as well as small, so that a small error in the position of a sensor 24 does not interfere with the cancellation of the residual magnetic field when taking the magnetic gradient measurement. The effectiveness of the arrangement of the coil 12 depends in part on the dimensions of the two PC boards 14, 16, and the separation distance between the boards 14, 16. The ac fields at the locations of the sensors 24 are smallest and most nearly uniform if the sensors 24 are located as close as possible to the plane midway between the two current sheets, the separation between the current sheets is as small as possible compared with their length and width, and the length and width of the current sheets is as large as possible compared with the distance between sensors 24.

Each of these key dimensions is affected by other considerations. First, as discussed above, the length of the gradiometer baseline must be comparable to the distance from the sensors 24 to the source of the magnetic susceptibility anomaly. In the case where the invention is used to screen the orbit of the eye of a patient, this is the distance from the primary sensors to the most distant point in the orbit of the eye. The current sheets must be as long and wide as possible compared with this baseline, while the PC boards 14, 16 must be small enough that they can be centered at a point next to the patient's eye without the edges of the PC boards 14, 16 interfering with other parts of the patient's body, such as the shoulders. The separation between the current sheets must be large enough to accommodate the physical size of the magnetic sensors 24.

Further, the separation must be large enough to eliminate the "graininess" of the applied field which results from the electric current distribution pattern on the PC boards 14, 16. To approximate a uniform sheet of current, current is passed through a set of parallel traces 18 on each PC board 14, 16. Since there must be some finite separation between the traces, the resulting electric current distribution is not completely uniform, but instead has a periodic variation in the direction transverse to the traces 18, the x direction in FIGS. 1 and 2. The resulting magnetic field has a corresponding periodic variation, which is most pronounced immediately adjacent to the traces 18, and which decays with increasing distance from the current sheets. Because of this spatial variation, the magnetic fields in the region between the two current sheets are not completely canceled out. In addition, since this spatial variation occurs on a fine scale, relatively small errors in the position of a primary sensor 24 can cause significant changes in the amount of ac applied field seen by that sensor 24.

In designing the excitation device 10 for a given application, a goal must be set for the degree to which the background signal due to the ac applied field must be suppressed by the field cancellation coils and the magnetic gradient measurements. The magnetic sensors 24 are then placed far enough from each current sheet so that the periodically varying component of the ac field, or "graininess", is smaller than the acceptable residual fields. This limit on the separation of the sensors 24 from the current sheets then determines how close together the two printed-circuit boards 14, 16 can be placed.

For example, a reasonable goal for ocular screening would be to suppress the applied fields so that the ac signal seen by the primary sensors is roughly a factor of $10^2$ or $10^3$ less than that corresponding to the ac field amplitude actually applied to the eye. The "graininess" or spatial variation of the fields near the parallel traces 18 has a complex mathematical form. However, the dominant contribution has an exponential decay in the direction perpendicular to the current sheet, and a sinusoidal variation in the direction transverse to the traces 18. That is, the "graininess" of the field can be expressed roughly by the relation:

$$\frac{\delta B}{B_0} \approx \frac{\Delta x}{l} \cos\left(\frac{2\pi x}{l}\right) e^{-2\pi z/l},$$

where $\delta B$ is the varying component of the magnetic field, $B_0$ is the spatially averaged value of the magnetic field, $\Delta x$ is the separation between the traces 18, l is the period of the pattern of traces 18, z is the perpendicular distance from the current sheet, and x is the position coordinate in the direction transverse to the traces 18. In a typical case, l might be 2.5 mm, and $\Delta x$ might be 0.25 mm. The magnitude of these dimensions may be dictated by the degree of precision with which the PC boards can be manufactured. If it is desired to have $\delta B/B_0$ less than 1%, then, z, the distance from the magnetic sensors 24 to the current sheets, must be greater than 1.83 mm.

As mentioned above, the magnetic sensors 24 are placed between the two PC boards 14, 16, in the region of nearly zero applied magnetic field. To minimize measurement errors due to the residual applied field, the excitation coils 12 are laid out in a symmetrical way, and the magnetic sensors 24 are placed strategically to exploit this symmetry. More specifically, the current paths 18 and return paths 20 on each PC board 14, 16 are split into two spiral-like coils, arranged symmetrically about the y axis which runs down the center of the PC board. Consequently, the magnetic field produced by each PC board 14, 16 is symmetrical with respect to reflection through the y axis. The spiral coils 12 are also shaped so that the magnetic field is nearly symmetrical with respect to the x axis which lies in the center of the PC board in the direction perpendicular to the y axis. Four magnetic sensors 24 can be used, with the sensors 24 located at the four corners of a square, symmetrically disposed with respect to the x and y axes. With this arrangement, the applied field is not only small, but approximately the same for all the sensors 24. The sensor 24 at one corner is used as the reference sensor in a Three-Sensor Gradiometer, while the three other sensors 24 are used as primary sensors. The sensors 24 are connected to the appropriate TSG circuitry 30, where differences in the outputs of the three primary sensors are processed to measure gradients of the magnetic field of the ferromagnetic foreign body. The output 32 of the TSG circuitry 30 is connected to a computer processor 34.

In the case where the sensor 24 at each corner is a three-axis magnetometer, measuring all three components of the magnetic field, the outputs of this circuitry yield all five components of the magnetic gradient tensor. The gradient outputs can then be processed using the Frahm-Wynn algorithm, as is well known in the art, to locate and characterize the FFB.

The arrangement described above uses a single set of excitation coils 12 to make magnetic response measurements with the applied magnetic field oriented in one direction. Making a single measurement with such a "single coil" instrument may not detect a long, slender piece of ferromagnetic material whose long axis is perpendicular to the applied magnetic field. As an example, assume an excitation coil 12 having current flow in the y direction, and assume that the applied magnetic field at the location of the FFB is oriented, for instance, parallel to the x axis. If the FFB is long and slender, and if its long axis is oriented orthogonal to the x direction, the resultant field from the FFB may not be great enough to be detected by the sensors 24.

A more versatile apparatus results from using two excitation coils 12 in a "double coil" instrument, to produce magnetic fields oriented in two orthogonal directions. A first excitation coil 12 has the same design as shown in FIG. 1 or FIG. 2, including traces 18, 20 on two parallel PC boards 14, 16 to approximate the effect of two parallel, uniform sheets of current flowing in the y direction. A second excitation coil 12 is identical in design to the first coil 12, and the second coil 12 is accommodated on the surfaces of the same two PC boards 14, 16, but it is oriented at right angles to the first excitation coil 12. This second excitation coil 12 approximates the effect of two parallel, uniform sheets of current flowing, for example, in the x direction.

The two excitation coils 12 are comprised of two independent sets of traces which are accommodated on the PC boards 14, 16, using standard multilayer technology with an insulating layer between the two sets of traces. During magnetic response measurements, the two excitation coils 12 are supplied with ac power which is phase shifted by 90 degrees, so that the net magnetic field rotates continuously in the x-y plane, the plane parallel to the surfaces of the PC boards 14, 16. Changes in the responsive magnetic field produced by the FFB are measured as a function of this revolving applied magnetic field. This will detect the presence of any FFB having a significant dimension in the x-y plane.

Figure 4:
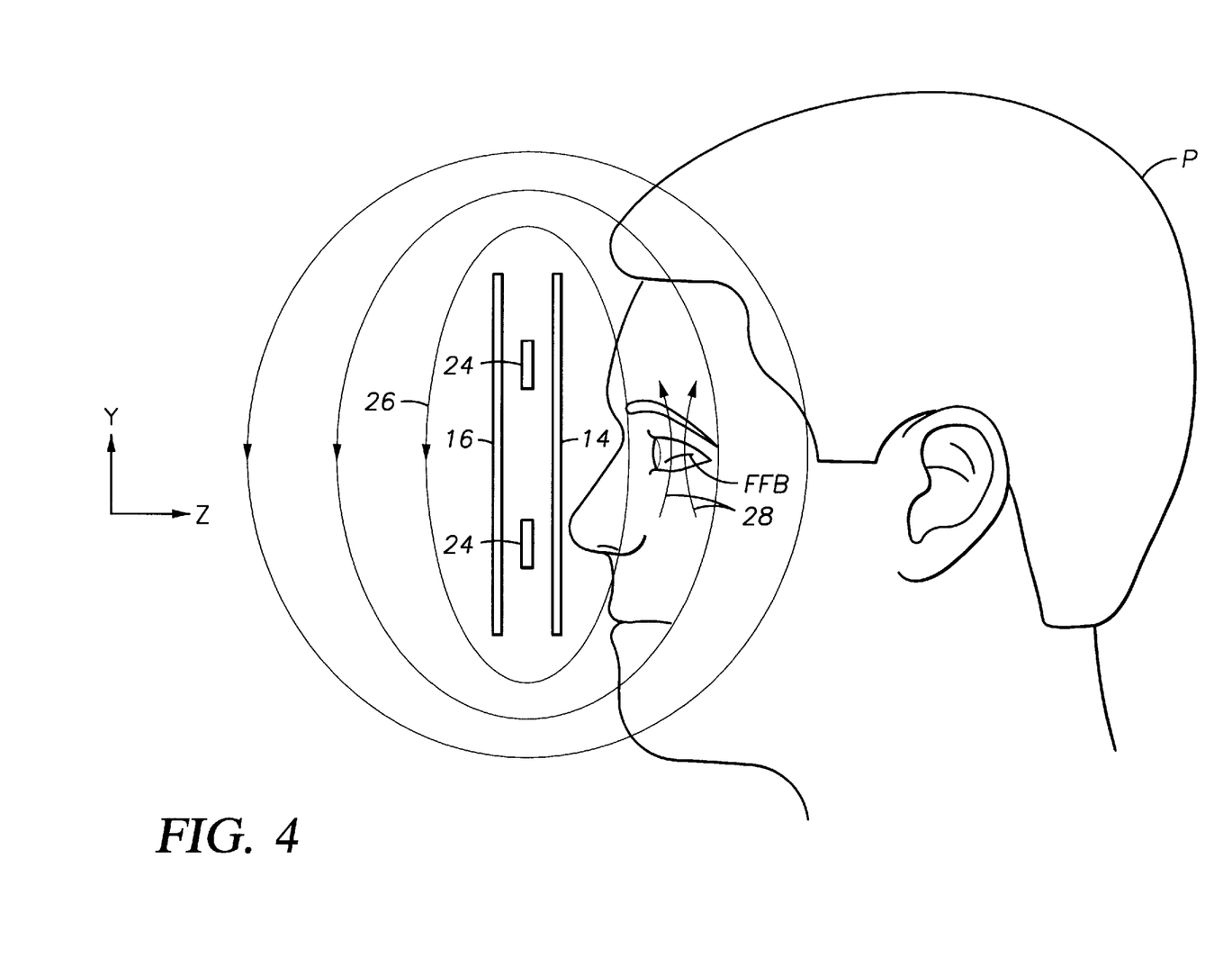
FIG. 4 is a side view of a patient, showing the invention in use.

By way of example, as shown in FIG. 4, the "double coil" apparatus can be used to detect FFB's in the eye of a patient. The PC boards 14, 16 containing the double excitation coils 12 are positioned approximately parallel to the forehead of the patient P, with the magnetic sensors 24 placed midway between the PC boards 14, 16. The entire instrument is placed as close as possible to the eye. Only two of the four sensors 24 are seen in this view. An applied magnetic field 26 is created by the second excitation coil 12 discussed above, in the PC boards 14, 16. The second excitation coil 12, which would create the magnetic field 26 shown in this view, is the excitation coil which has its current flow in the x direction, perpendicular to the page toward the viewer. A responsive magnetic field 28 is shown, resulting from the response of the FFB to the applied ac magnetic field 26.

A similarly shaped applied ac magnetic field (not shown) would be oriented orthogonally to the field 26. This additional applied magnetic field would be created by the first excitation coil 12 discussed above, which has current flowing in the y direction. The additional applied field would cause an additional responsive field (not shown) around the FFB. In this position of the instrument, the two orthogonal excitation coils produce an applied magnetic field which lies roughly parallel to the forehead. As the two excitation coils 12 are energized with a 90 degree phase angle, this applied field will rotate about the z axis. The sensors 24 will detect changes in the responsive magnetic fields around ferrous objects which respond to the applied magnetic fields in this plane. The signals from the sensors 24 will be processed as described above to measure the magnetic gradient of the FFB.

As mentioned above, long, slender objects with their long axes perpendicular to the plane of the applied field may not be detected. Such objects can be detected, however, regardless of orientation, by making measurements at two different positions of the "double coil" instrument. For example, with the instrument orientation shown in FIG. 4, the applied magnetic fields from both of the excitation coils would be essentially perpendicular to the z axis, in the area of the patient's eye. A long, slender object in the eye, with its axis essentially parallel to the z axis, might not be detected, since the axis of the FFB would be essentially perpendicular to the applied magnetic fields from both of the excitation coils. Therefore, to detect ferromagnetic bodies in the eye, measurements are made with two orientations of the sensing instrument. To detect such objects, a second measurement is made with the double excitation coils 12 oriented roughly parallel to the side of the face, with the magnetic sensors 24 again as close as possible to the eye. In this position, the magnetic field has a substantial component which would be parallel to the z axis, and parallel to the axis of the FFB. this magnetic-field component will produce a maximum magnetic signature for long, narrow objects oriented essentially parallel to the z axis.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for screening a host for the presence of a ferromagnetic body, said apparatus comprising:
    an excitation device for applying an alternating current magnetic field to a selected region of a host;
    a sensing device for sensing a changing magnetic susceptibility response of matter within said selected region of the host, and for generating an electrical signal indicating the occurrence of said changing magnetic susceptibility response; and
    a computing device for analyzing said signal from said sensing device to locate and characterize any magnetic susceptibility anomaly found within said selected region of the host, to indicate the presence of any ferromagnetic body;
    wherein said sensing device comprises at least one magnetoresistive sensor.

2. An apparatus for screening a host for the presence of a ferromagnetic body, said apparatus comprising:
    an excitation device for applying an alternating current magnetic field to a selected region of a host;
    a sensing device for sensing a magnetic susceptibility response of matter within said selected region of the host, and for generating an electrical signal indicating the occurrence of said magnetic susceptibility response; and
    a computing device for analyzing said signal from said sensing device to locate and characterize any magnetic susceptibility anomaly found within said selected region of the host, to indicate the presence of any ferromagnetic body;
    wherein:
        said excitation device comprises an applied field coil connected to an alternating current source, said field coil being designed to create a first zone of a finite magnetic field, within said selected region of the host, and a second zone of substantially zero magnetic field, outside said selected region; and
        said sensing device comprises at least one sensor, said at least one sensor being positioned within said second zone of substantially zero magnetic field.

3. An apparatus for screening a host for the presence of a ferromagnetic body said apparatus comprising:
    an applied field coil connected to an alternating current source, said field coil being designed to create a first zone of a finite alternating magnetic field, within a selected region of a host and said field coil being designed to create a second zone of substantially zero magnetic field, outside said selected region;
    a sensing device for sensing a magnetic susceptibility response of matter within said first zone of a finite alternating magnetic field, and for generating an electrical signal indicating the occurrence of said magnetic susceptibility response, said sensing device comprising at least one sensor positioned within said second zone of substantially zero magnetic field; and
    a computing device for analyzing said signal from said sensing device to locate and characterize any magnetic susceptibility anomaly found within said selected region of the host, to indicate the presence of any ferromagnetic body;
    wherein said applied field coil comprises:
        two parallel flat coils of conductor material, said flat coils approximating two parallel flat uniform sheets of current; and
        a connecting circuit connecting said two flat coils, causing current to flow in identical directions at corresponding locations in said two flat coils;
    wherein said first zone of said magnetic field is situated outside said flat coils; and
    wherein said second zone of substantially zero magnetic field is situated between said flat coils.

4. An apparatus for screening a host for the presence of a ferromagnetic body, said apparatus comprising:
    an excitation device for applying an alternating current magnetic field to a selected region of a host;
    a sensing device for sensing a magnetic susceptibility response of matter within said selected region of the host, and for generating an electrical signal indicating the occurrence of said magnetic susceptibility response; and
    a computing device for analyzing said signal from said sensing device to locate and characterize any magnetic susceptibility anomaly found within said selected region of the host, to indicate the presence of any ferromagnetic body;
    wherein said sensing device comprises:
        at least two primary sensors for sensing a magnetic gradient resulting from a magnetic susceptibility anomaly, said primary sensors being optimized for low noise;
        a reference sensor for sensing the magnetic background, including said applied magnetic field, said reference sensor being optimized for wide range;
        a first compensation coil around said reference sensor for canceling the effects of the magnetic background on said reference sensor;
        an additional compensation coil around each of said at least two primary sensors for canceling the effects of the magnetic background on said primary sensors; and
        a feedback loop for monitoring the output of said reference sensor and applying current to said first compensation coil to maintain said reference sensor at a constant field, and for applying the same current to said additional compensation coils, to eliminate the effect of the magnetic background on said primary sensors.

5. A method for screening a host for the presence of a ferromagnetic body, said method comprising:
    providing an alternating current excitation device, a magnetic susceptibility sensing device, and a computing device for analyzing signals from said sensing device;
    applying an alternating current magnetic field to a selected region of a host, with said excitation device;

sensing magnetic susceptibility responses of matter within said selected region of the host, with said sensing device, and generating signals indicative of said magnetic susceptibility responses; and analyzing said signals from said sensing device to locate and characterize any magnetic susceptibility anomaly found within said selected region of the host, to indicate the presence of any ferromagnetic body;

wherein said application of a magnetic field to said selected region of the host comprises:

creating a first zone of a finite magnetic field within said selected region of the host, and a second zone of substantially zero magnetic field outside said selected region; and positioning said sensing device within said second zone of substantially zero magnetic field.

6. A method as recited in claim 5, wherein said creation of a dual zone applied magnetic field comprises:

approximating two parallel flat uniform sheets of current with two parallel flat coils of conductor material;

connecting said two flat coils so as to cause current to flow in identical directions at corresponding locations in said two flat coils;

creating said first zone of said magnetic field outside said two flat coils; and creating said second zone of substantially zero magnetic field between said two flat coils.

7. A method for screening a host for the presence of a ferromagnetic body, said method comprising:

providing an alternating current excitation device, a magnetic susceptibility sensing device comprising at least two sensors, and a computing device for analyzing signals from said sensing device;

applying an alternating current magnetic field to a selected region of a host, with said excitation device;

placing said at least two sensors symmetrically with respect to said applied magnetic field, so as to sense substantially identical applied magnetic fields;

canceling the effect of the magnetic background, including said applied field, on said at least two sensors;

sensing magnetic susceptibility responses of matter within said selected region of the host, with said sensing device, and generating signals indicative of said magnetic susceptibility responses; and analyzing said signals from said sensing device to locate and characterize any magnetic susceptibility anomaly found within said selected region of the host, to indicate the presence of any ferromagnetic body;

wherein said at least two sensors are high sensitivity sensors, and said sensing device further comprises a wide range reference sensor, at least three compensation coils, and a feedback loop, said background cancellation comprising:

sensing the magnetic background, including said applied magnetic field, with said reference sensor;

monitoring the output of said reference sensor and applying a compensating current to a first said compensation coil to maintain said reference sensor at a constant field;

applying said compensating current to additional said compensation coils, to eliminate the effect of the magnetic background on said high sensitivity sensors; and sensing a magnetic gradient resulting from a magnetic susceptibility anomaly, with said high sensitivity sensors.

8. A method for screening a host for the presence of a ferromagnetic body, said method comprising:

providing an alternating current excitation device, a magnetic susceptibility sensing device, and a computing device for analyzing signals from said sensing device;

applying an alternating current magnetic field to a selected region of a host, with said excitation device;

moving said alternating current excitation device and said magnetic susceptibility sensing device relative to said selected region of the host;

sensing magnetic susceptibility responses of matter within said selected region of the host, with said moving sensing device, and generating a map of signals indicative of said magnetic susceptibility responses; and analyzing said signal map generated by said sensing device to locate in three dimensions any magnetic susceptibility anomaly found within said selected region of the host and to identify the magnitude and orientation of a magnetic susceptibility anomaly resulting from any ferromagnetic body.

* * * * *